United States Patent
Caporizzo et al.

[19]

[11] Patent Number: 6,014,547
[45] Date of Patent: Jan. 11, 2000

[54] SYSTEM FOR ENHANCING THE PERFORMANCE OF A CATV SETTOP TERMINAL

[75] Inventors: Louis Caporizzo, North Wales; Christine Johnson, Chalfont, both of Pa.

[73] Assignee: General Instrument Corporation, Horsham, Pa.

[21] Appl. No.: 08/847,697

[22] Filed: Apr. 28, 1997

[51] Int. Cl.[7] .............................. H04H 1/02; H04B 1/10; H04N 7/10; H04N 5/50

[52] U.S. Cl. .............................. 455/6.2; 348/10; 348/11; 348/731; 455/266; 455/234.1; 455/180.1; 455/188.1; 455/307

[58] Field of Search .............................. 348/10, 11, 607, 348/726, 731, 678, 6, 7, 12, 13, 192, 193, 725; 455/6.2, 295, 234.1, 4.1, 4.2, 6.1, 6.3, 266, 5.1, 3.1, 200.1, 177.1, 306, 307; 333/28 R, 18; 375/229, 350; 364/724.011, 724.06, 724.08; H04N 5/44, 5/52, 7/16, 7/10, 7/173

[56] References Cited

U.S. PATENT DOCUMENTS

| | | |
|---|---|---|
| 3,781,703 | 12/1973 | Duty .............................. 330/52 |
| 3,935,534 | 1/1976 | Lewis et al. .............................. 325/308 |
| 4,245,350 | 1/1981 | Moore .............................. 455/180 |
| 4,472,685 | 9/1984 | Dutasta .............................. 329/50 |
| 4,520,507 | 5/1985 | Moon .............................. 455/3 |
| 4,571,560 | 2/1986 | Dobrovolny .............................. 348/11 |
| 4,827,511 | 5/1989 | Masuko .............................. 380/15 |
| 4,850,038 | 7/1989 | Shibata et al. .............................. 455/315 |
| 4,979,230 | 12/1990 | Marz .............................. 455/3 |
| 5,014,309 | 5/1991 | West, Jr. .............................. 380/7 |
| 5,083,205 | 1/1992 | Arai .............................. 358/140 |
| 5,155,590 | 10/1992 | Beyers, II et al. .............................. 358/86 |
| 5,179,726 | 1/1993 | Moon .............................. 455/180.4 |
| 5,231,660 | 7/1993 | West, Jr. .............................. 380/7 |
| 5,293,633 | 3/1994 | Robbins .............................. 455/3.1 |
| 5,528,633 | 6/1996 | Halik et al. .............................. 375/326 |
| 5,745,159 | 4/1998 | Wax et al. .............................. 348/8 |
| 5,752,179 | 5/1998 | Dobrovolny .............................. 455/266 |

*Primary Examiner*—John W. Miller
*Attorney, Agent, or Firm*—Volpe and Koenig, P.C.

[57] ABSTRACT

A system for use with a CATV settop terminal measures the input RF carrier signal power level at several frequencies within the CATV RF input bandwidth upon system power-up. The system utilizes these measurements to selectively equalize and process the RF input signal depending upon the carrier frequency selected and the desired signal level to be input to the RF tuner. The system refines the signal level by specifically measuring the signal level of the selected carrier frequency. The system further improves RF tuner performance by dynamically limiting the bandwidth input to the RF tuner depending upon the selected carrier frequency.

6 Claims, 6 Drawing Sheets

SYSTEM FOR ENHANCING THE PERFORMANCE OF A CATV SETTOP TERMINAL

BACKGROUND OF THE INVENTION

1. Field of the Invention

This invention generally relates to cable television (CATV) communication systems. More particularly, the invention relates to a CATV settop terminal which includes a system for enhancing the performance of the RF tuner.

2. Description of the Related Art

The CATV transmission spectrum typically comprises a bandwidth of frequencies up to 1000 MHz. During transmission of signals over the CATV network between the headend and the settop terminals, the higher frequencies experience greater attenuation than the lower frequencies. To compensate for the unequal attenuation, CATV network operators install devices throughout the CATV network to periodically equalize and amplify the signals as they are transmitted over the network. However, once the signal is output from the last active component in the transmission network, such as a line amplifier, no compensation for the unequal attenuation is provided. When line extenders are introduced or when a subscriber is located a long distance from the tap, large inequalities develop between the strength of signals at lower frequencies and those at higher frequencies. This degrades the performance of the RF tuner.

A second problem that reduces the performance of the RF tuner is the introduction of second and higher order distortions caused by the plurality of input carrier frequencies. As CATV network operators offer more channels over their networks, the bandwidth of the CATV network continues to expand. This results in an increase in the number of input carrier frequencies, which further degrades the performance of the RF tuner due to second and higher order distortions.

Accordingly, there exists a need for an inexpensive method to improve RF tuner performance in dual conversion CATV settop terminals.

SUMMARY OF THE INVENTION

The present invention comprises a system for use with a CATV settop terminal which measures the input RF carrier signal power level at several frequencies within the CATV RF input bandwidth upon system power-up. The system utilizes these measurements to selectively equalize and process the RF input signal depending upon the carrier frequency selected and the desired signal level to be input to the RF tuner. The system refines the signal level by specifically measuring the signal level of the selected carrier frequency. The system further improves RF tuner performance by dynamically limiting the bandwidth input to the RF tuner depending upon the selected carrier frequency.

Accordingly, it is an object of the present invention to provide a settop terminal with improved RF tuner performance.

Other objects and advantages will become apparent to those skilled in the art after reading the detailed description of the preferred embodiment.

DESCRIPTION OF THE PREFERRED EMBODIMENTS

The preferred embodiment will be described with reference to the drawing figures where like numerals represent like elements throughout.

Figure 1:
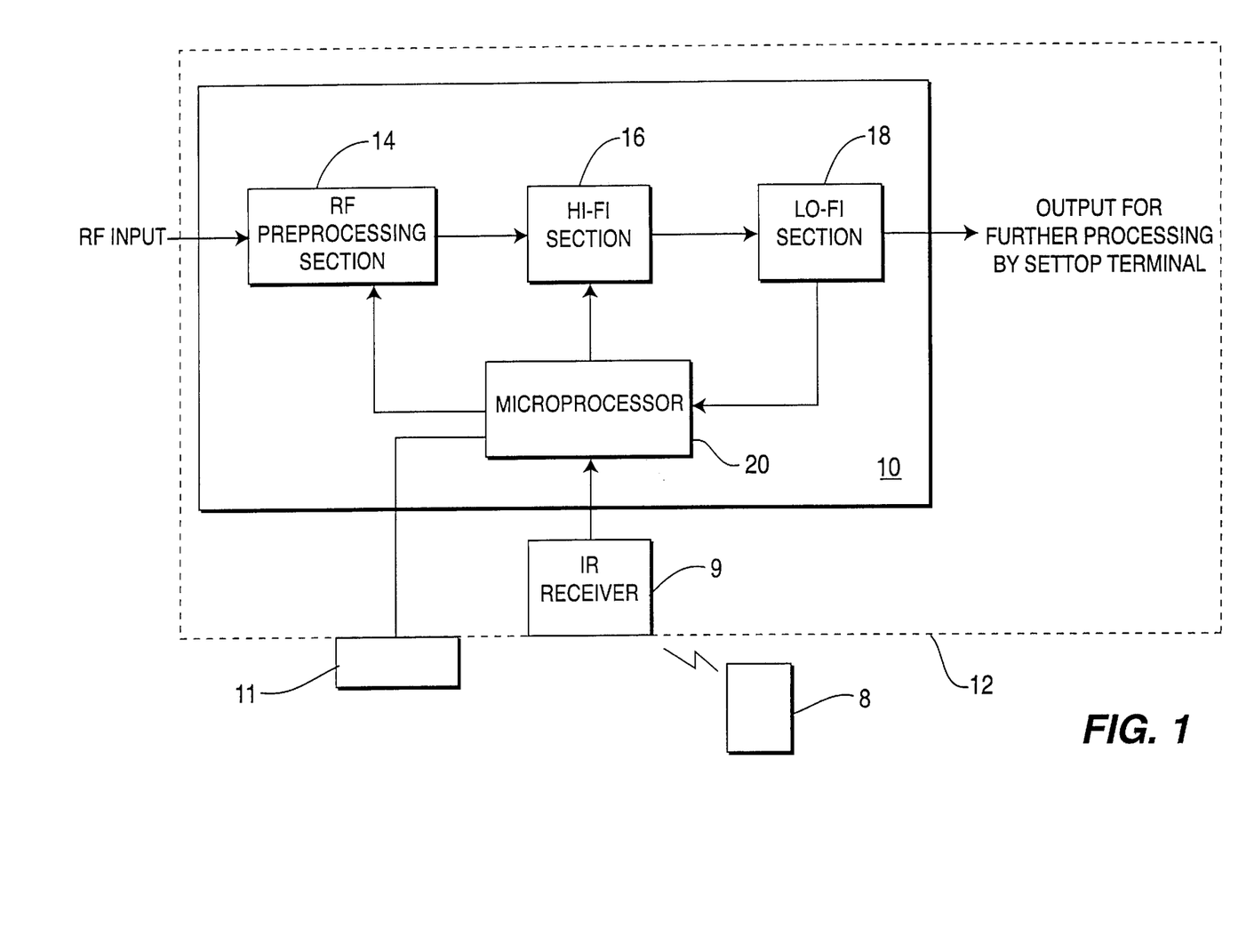
FIG. 1 is a block diagram of the preferred embodiment of the settop terminal present invention.

FIG. 1 is a block diagram of a system 10 made in accordance with the teachings of the present invention for enhancing RF tuner performance of a dual conversion settop terminal 12. The settop terminal 12 is responsive to the selection of a particular channel by a consumer for viewing and listening. A consumer selects a desired channel using an input means, such as an infrared (IR) remote transmitter 8, which outputs to an IR receiver 9. Alternatively, a touchpad 11, keyboard (not shown) or any other type of input device may be used. In response to the selection, the settop terminal 12 tunes to the RF carrier frequency associated with the selected channel and removes the carrier frequency. Audio and video content are then processed in a manner well known to those skilled in the art for viewing and listening by the consumer.

The system 10 generally comprises a radio frequency (RF) preprocessing section 14, a high-intermediate frequency (HI-IF) section 16, a low-intermediate frequency (LO-IF) section 18 and a microprocessor 20. The RF preprocessing section 14 and the HI-IF section comprise what is typically referred to as a tuner 11.

The RF preprocessing section 14 is coupled to the CATV transmission network via the RF input. The RF preprocessing section 14 accepts the entire RF input spectrum and preprocesses a select bandwidth of the spectrum as will be described in detail hereinafter. The HI-IF section 16 accepts the preprocessed bandwidth from the RF preprocessing section 14 and tunes to the carrier frequency corresponding to the channel selected by the consumer. The carrier frequency is upconverted, filtered and downconverted for output to the LO-IF section 18.

The LO-IF 18 section further filters the IF signal, measures the signal level and removes the video and audio information from the IF signal. The baseband video and audio signal is forwarded for further processing by the settop terminal 12 in a manner that is well known to those skilled in the art. A control signal is also output by the LO-IF section 18 to the microprocessor 20, which provides overall control of the RF preprocessing section 14 and the HI-IF section 16.

The RF spectrum transmitted over the CATV transmission network is a wideband RF signal, extending from approximately 50 to 1,000 MHz. As the wideband signal is transmitted from the headend of the CATV system to the plurality of settop terminals, the frequencies at the lower end of the spectrum will experience different propagation loss rates than the frequencies at the higher end of the spectrum. At the input to a settop terminal 12, therefore, the signal level of the lower frequencies may be much greater than the higher frequencies.

Figure 2:
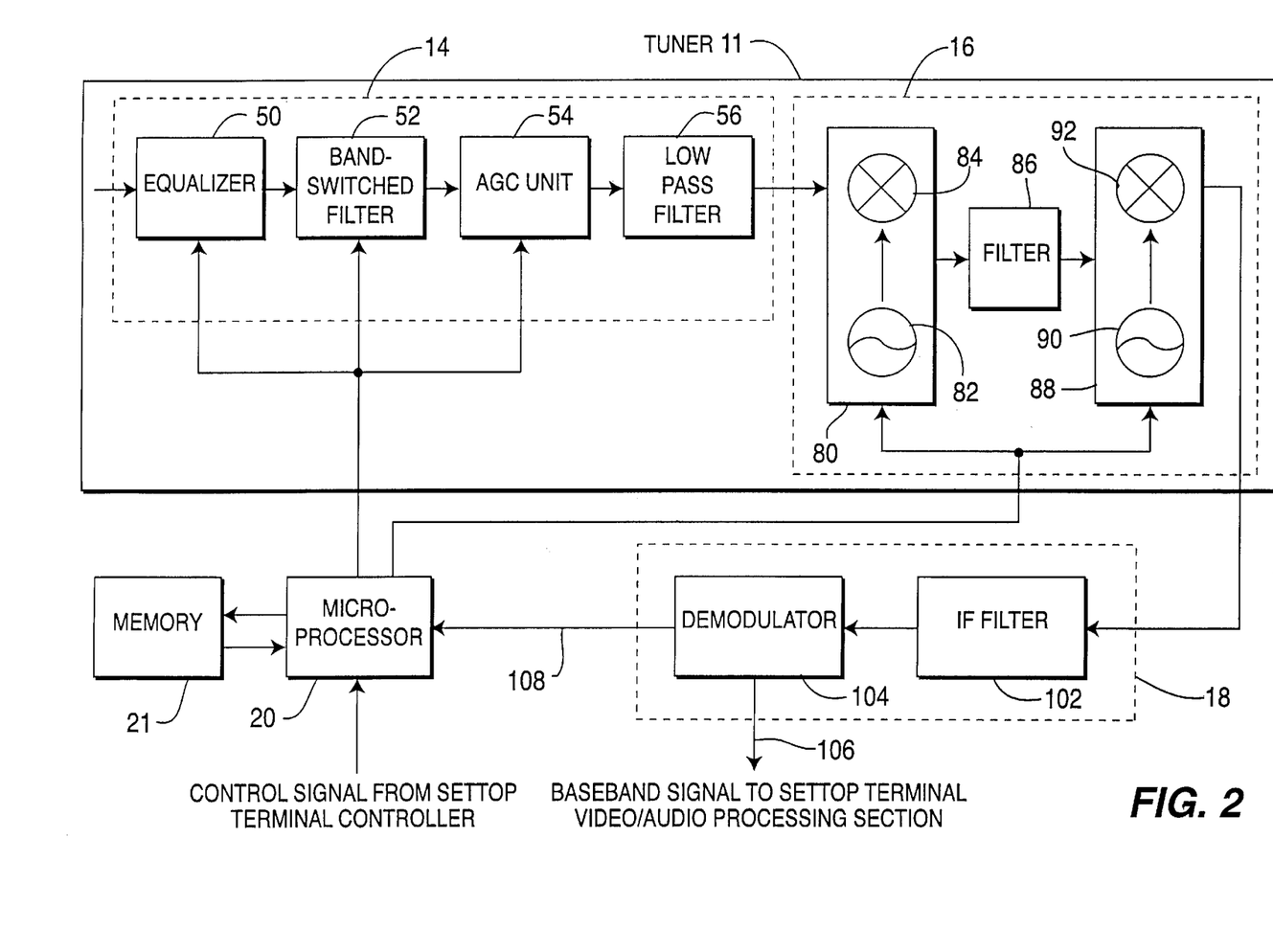
FIG. 2 is a detailed block diagram of the system of the present invention for enhancing the performance of a CATV settop terminal.
Figure 3:
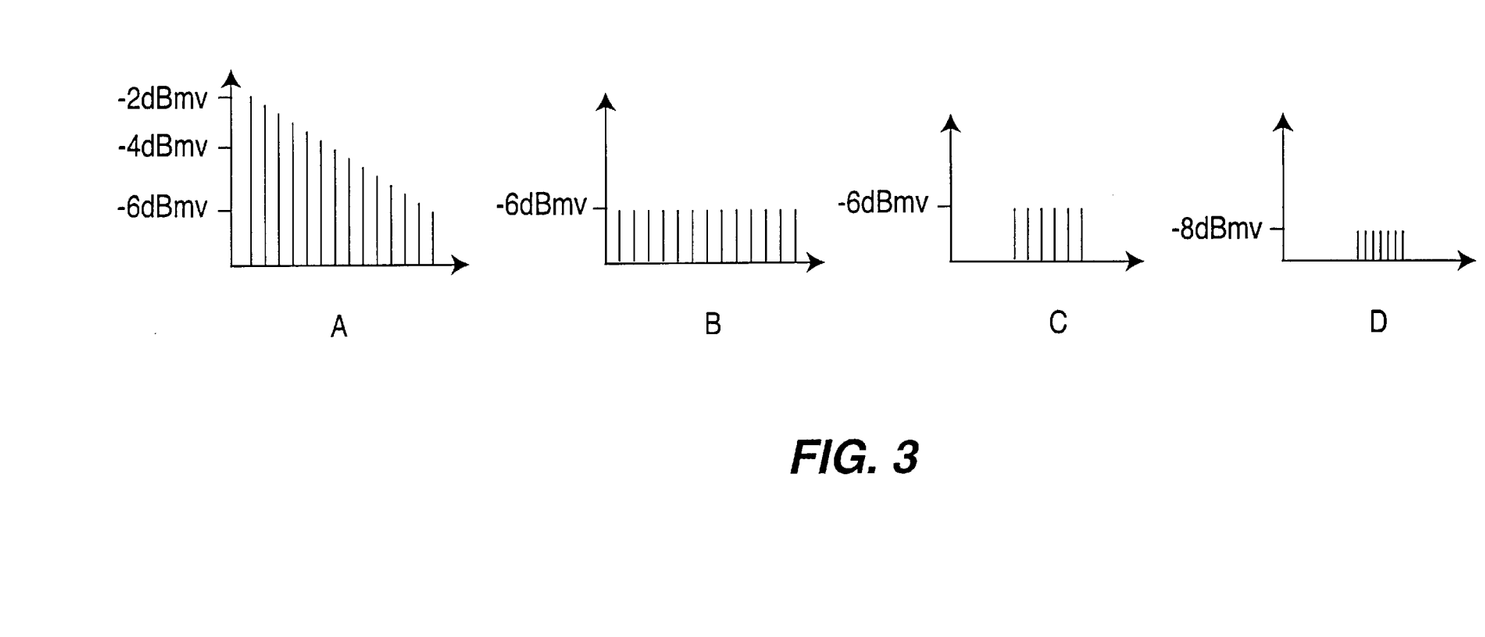
FIGS. 3A–3D are signal diagrams of the processing of the input RF spectrum.

Referring to FIG. 2, the RF preprocessing section 14 includes an equalizer 50, a band-switched filter 52, an automatic gain control (AGC) unit 54 and a lowpass filter 56. The equalizer 50 compensates for the difference in the signal level between the lower frequencies and the higher frequencies by attenuating the frequencies having a higher signal level to the same level as the frequencies having a lower signal level. The result of equalization can be seen with reference to FIGS. 3A and 3B. Prior to equalization, since the higher frequencies experience more attenuation in transmission than the lower frequencies, the higher frequencies have a lower signal level at the input of the equalizer 50 (FIG. 3A). After equalization, whereby the signal level of the lower frequencies has been attenuated to the same signal level of the higher frequencies, the entire bandwidth has the same signal level (FIG. 3B).

Figure 4:
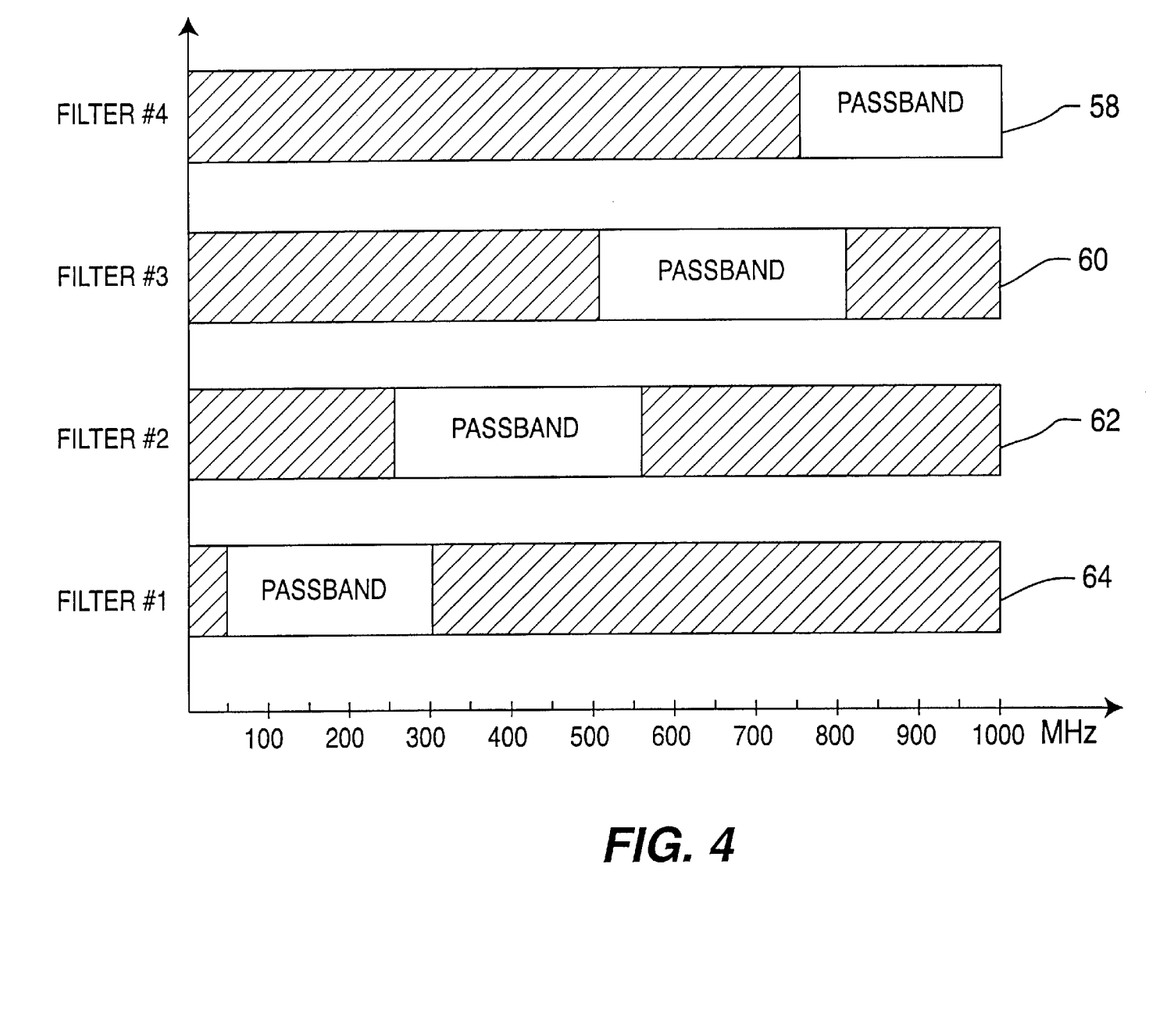
FIG. 4 is a diagram of the bandwidth of each individual filter within the band-switched filter.

The output of the equalizer 50 is input into the band-switched filter 52. Referring to FIG. 4, the band-switched filter 52 comprises a plurality of individual band-pass filters 58, 60, 62, 64 which are selectively activated, depending upon the channel, and thus carrier frequency, selected for viewing by the subscriber. Each band-pass filter 58, 60, 62, 64 passes those frequencies falling within a selected portion of the RF spectrum and attenuates all frequencies falling outside of the passband. Although four band-pass filters 58, 60, 62, 64 are shown in FIG. 4, a greater or lesser number of filters may be employed, depending upon the application and number of available channels.

The effect of the band-switched filter 52 using the second filter 62 upon the output of the equalizer 50 will be explained with reference to FIGS. 3B and 3C. The band-switched filter 52 passes only a portion of the input bandwidth. Accordingly, when the equalized output of FIG. 3B is input into the band-switched filter 52, an output having a reduced bandwidth as shown in FIG. 3C is obtained. This has a beneficial impact on the performance of the HI-IF section 16. Intermodulation distortion typically exists throughout the transmitted RF spectrum. As a portion of the RF spectrum is selected and further processed by a settop terminal, the intermodulation distortion increases. As a result of the bandlimiting process, which reduces the bandwidth of the RF spectrum and the number of RF carrier frequencies seen at the input to the HI-IF section 16 of the tuner 11, the increase in intermodulation distortion introduced by the settop terminal 12 is significantly reduced.

Referring again to FIG. 2, the output of the band-switched filter 52 is input into the AGC unit 54 which further attenuates or amplifies the signal to a desired level. For example, as shown in FIG. 3C, if the output from the band-switched filter 52 is at a level of −6 dBmv and it is desired to have a signal level input to the HI-IF section 16 of −8 dBmv, the signal level must be attenuated by an additional 2 dBmv as shown in FIG. 3D. The level input to the HI-IF section 16 may also be selectively adjusted to minimize distortions.

Referring again to FIG. 2, the output from the AGC unit 54 is passed through a low-pass filter 56 and is then input to the HI-IF section 16. The low-pass filter 56 band limits the input frequencies. As will be explained in detail hereinafter, the equalizer 50, the band-switched filter 52 and the AGC unit 54 are dynamically controlled by the microprocessor 20 to optimize the performance of the RF tuner 11.

The HI-IF section 16 generally comprises: 1) an upconverter 80; 2) a HI-IF filter 86; and 3) a downconverter 88. The upconverter 80 comprises a first adjustable local oscillator 82 and an upconverter mixer 84. The upconverter mixer 84 combines the signal output from the RF section 14 with the output of the first local oscillator 82 to upconvert the selected carrier frequency to a HI-IF frequency. Upconversion to the HI-IF frequency minimizes the interference to other television receivers by having the frequency of the first local oscillator 82 reside above any of the carrier frequencies. The HI-IF filter 86 filters the upconverted signal by providing rejection of other adjacent channel carriers outside the bandwidth of the filter 86.

The downconverter 88 includes a downconverter mixer 92 and a second local oscillator 90. The downconverter mixer 92 combines the HI-IF output signal with the output of the second adjustable local oscillator 90 to produce an output IF signal of 45.75 MHZ for the video carrier signal and 41.25 MHZ for the audio carrier signal to the LO-IF section 18.

The LO-IF section 18 includes an IF filter 102 and a demodulator 104. The IF filter 102 is a single channel filter which limits all unnecessary frequency components. The upper adjacent channel video carrier and lower adjacent channel sound carrier are attenuated at least 40–50 dB to eliminate visible disturbances in the picture. The output of the IF filter 102 is input into the demodulator 104 for video and sound IF carrier demodulation. The demodulator 104 measures the signal level of the video carrier and compares the video carrier level against a reference level to determine whether the video carrier level is too high or too low. If the video carrier level is at the proper level, (as determined by the reference level including tolerances), no further adjustments to the signal will be required. Accordingly, a baseband output signal 106, including the video and audio information, are forwarded for further processing by the settop terminal 12. This processing includes descrambling and upconversion of the video and sound information to a second RF carrier for input into a television. The processing techniques are well known to those skilled in the art and a detailed description is outside the scope of this invention.

If the video carrier level as seen at the input to the demodulator 104 is too high or too low, the demodulator 104 outputs a control signal 108 to adjust the AGC level as determined by the AGC unit 54. The control signal 108 may be input to the microprocessor 20 which controls the AGC unit 54 as shown in FIG. 2. The control signal 108 is analyzed by the microprocessor 20, which dynamically controls the equalizer 50, the band-switched filter 52 and the AGC unit 54 as will be described in greater detail hereinafter. Alternatively, the demodulator 104 may output a separate control signal directly to the AGC unit 54 to override the control signal sent from the microprocessor 20 and to perform AGC level refinement.

When a channel is selected by a consumer, the selection is converted by the microprocessor 20 into a corresponding voltage. This voltage is used to adjust the frequency of the first local oscillator 82 to select the carrier frequency which corresponds to the channel selected by the consumer.

Figure 5:
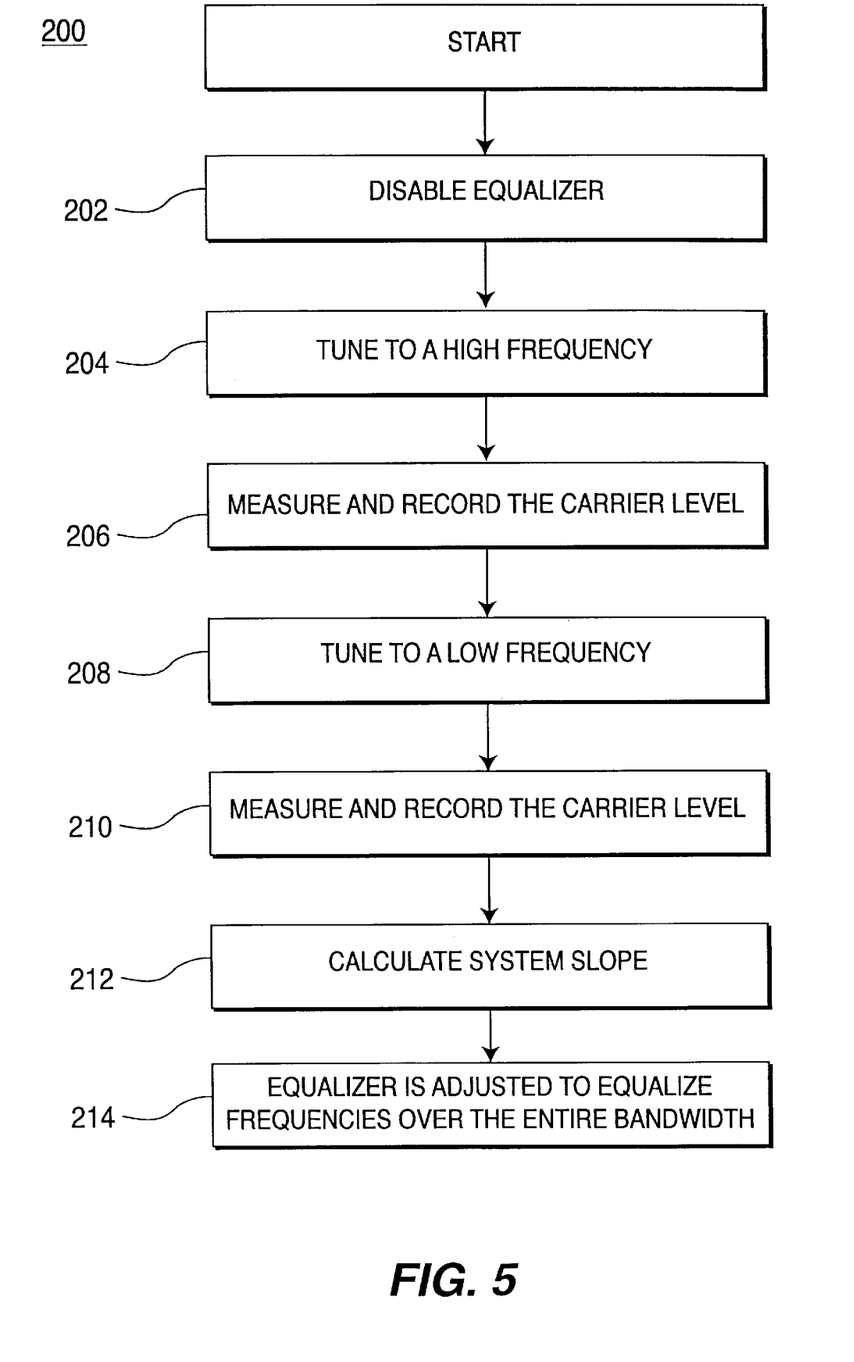
FIG. 5 is a flow diagram of the settop terminal in the setup mode.

The present invention operates in two modes: 1) power-up mode 200, and 2) active mode 400. Referring to FIG. 5, the operation of the present invention in the power-up mode 200 will be explained. Upon energizing the system 10, the microprocessor 20 disables the equalizer 50 so that the RF input may be analyzed (step 202). The microprocessor 20 controls the HI-IF section 16 to tune to a high carrier frequency ($x_2$) within the CATV bandwidth (step 204). The carrier signal level ($y_2$) at that frequency is measured at the demodulator 104 and recorded by the microprocessor 20 (step 206). The microprocessor 20 then controls the HI-IF section 16 to tune to a low carrier frequency ($x_1$) (step 208). The carrier signal level ($y_1$) at that frequency is measured at the demodulator 104 and recorded by the microprocessor 20 (step 210). It should be noted that the carrier signals that are measured are signals that are used to transmit "actual" video and audio information. Accordingly, no "pilot carriers" are required.

Using the aforementioned measurements, the system slope (m) is calculated by the microprocessor 20 (step 212) using the following equation:

$$y_2 - y_1 = m(x_2 - x_1) \quad \text{Equation (1)}$$

Assuming a linear slope (m) between the carrier signal level measured at the high and low frequencies:

$$y_2 = mx + b, \quad \text{Equation (2)}$$

the carrier signal level at any frequency may determined. In the preferred embodiment, the carrier signal level for a particular frequency is dynamically calculated as a channel is selected by the subscriber. Accordingly, when a channel is selected by a subscriber, the microprocessor 12 calculates the carrier signal level corresponding to that frequency and selectively adjusts the AGC unit 54 to provide the desired signal level for input into the HI-IF section 16.

In a first alternative embodiment, the microprocessor 20 may precalculate the carrier signal level and a corresponding attenuation for each carrier frequency transmitted over the CATV network, and store these values in memory 21, which is preferably non-volatile random access memory NVRAM.

In a second alternative embodiment, the slope may be set equal to zero and the actual level of each carrier may be measured. Whether the actual carrier signal level for each carrier frequency is measured, or the actual level for only several carrier frequencies is measured, the present technique provides a clear advantage over prior techniques which typically calculate an average for a plurality of carrier frequencies.

After the slope of the CATV network has been determined, the equalizer 50 is adjusted to equalize the frequencies over the entire bandwidth to provide a consistent carrier signal level output to the HI-IF section 16 (step 214). The power-up mode 200 may be entered periodically to ensure that the equalization, attenuation and gain control are optimally tailored to the current conditions of the CATV transmission network. Should the conditions of the CATV transmission network result in a change in the system slope, the equalizer 50 and the AGC unit 54 will be adjusted accordingly.

Figure 6:
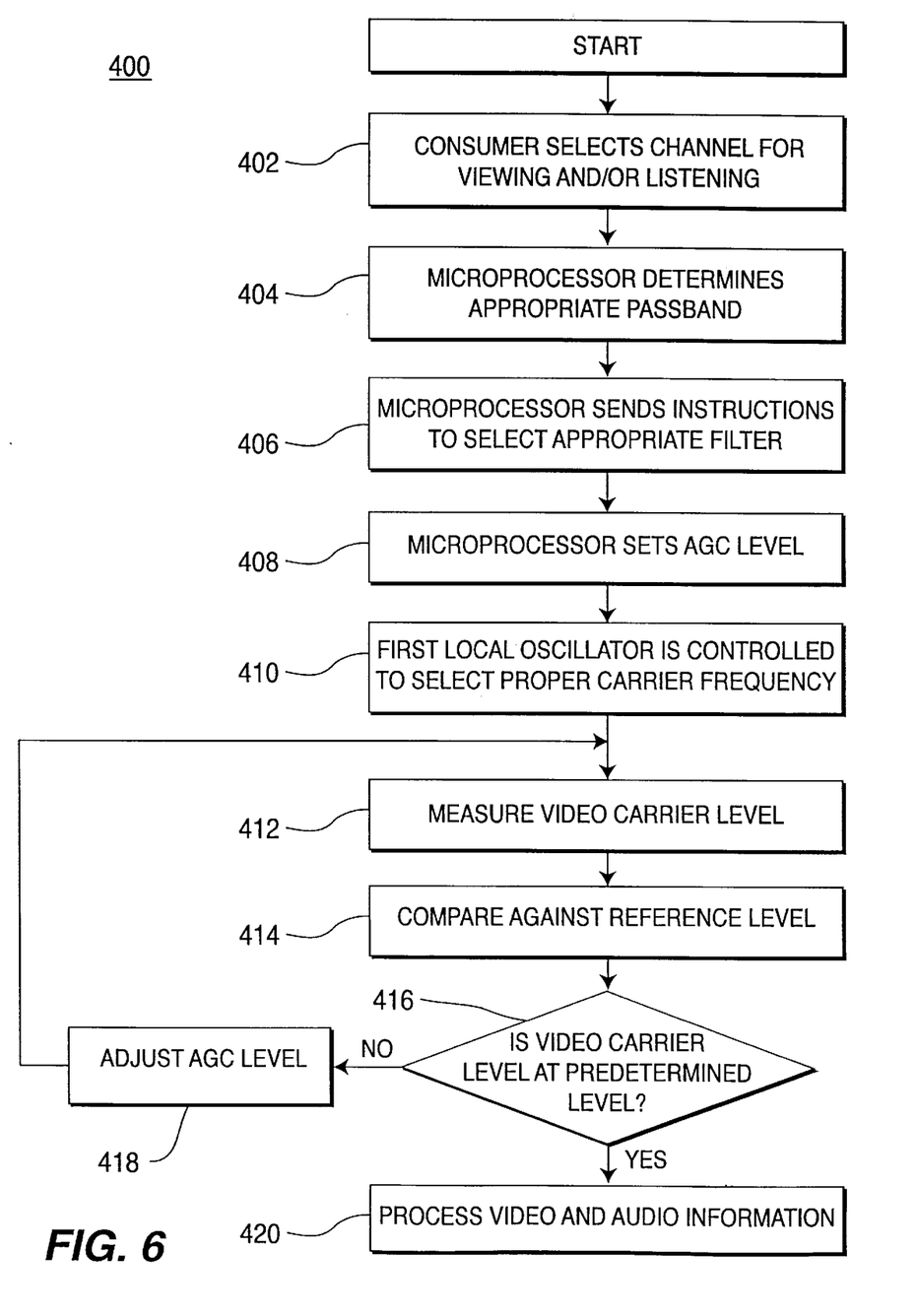
FIG. 6 is a flow diagram of the settop terminal in the active mode.

Operation of the system 10 in the active mode 400 will be explained with reference to FIG. 6. When the consumer selects a desired channel (step 402) the microprocessor 20 performs several functions. First, the microprocessor 20 determines within which passband the selected carrier frequency will fall (step 404) The microprocessor 20 then sends a control instruction to the band-switched filter 52 to select the filter having the appropriate passband (step 406). The signal level for the selected carrier frequency is calculated and the level of amplification or attenuation by the AGC unit 54 is adjusted (step 408) to provide an output to the HI-IF section 16 at the desired level. The output of the first local oscillator 82 is controlled to select the desired carrier frequency for upconversion to the HI-IF bandwidth (step 410). The demodulator 104 measures the video carrier level (step 412) and compares this level against a reference level (step 414). If the video carrier level is the same as the predetermined level, (including tolerances), (step 416), no further adjustments to the signal will be required. The video and audio baseband signal is then output to the settop terminal video and audio processing section for further processing (step 420) in a manner well known to those skilled in art. If the video carrier level is not at the predetermined reference level (step 416), the demodulator 104 outputs a control signal to refine the AGC level (step 418). Steps 412–418 are repeated until the carrier level is at the reference level.

The flexible architecture of the present invention may be utilized in an alternative embodiment to further increase the performance of the tuner 11. For example, many settop terminals 12 contain a frequency channel map which describe the frequency placement of all the channels on the CATV network. Once the slope for the entire cable plant has been determined as aforementioned, the bandpass filter which corresponds to the tuned frequency may be activated. Knowing the channels which exist in the portion of bandwidth spanned by the passband filter, the system 10 can measure the signal level at a low channel within the bandwidth and a high channel within the bandwidth to further optimize the slope calculation for that bandwidth. This further improves performance of the tuner 11.

Additionally, since the tuner 11 of the present invention can measure carrier signal level on a channel by channel basis, a more accurate algorithm to optimize slope across the RF input bandwidth may be utilized. For example, if the input carrier levels displayed a parabolic shape, the microprocessor 20 may be programmed to implement an algorithm which is the inverse of the parabolic shape, thereby resulting in a flat RF response which is input into the HI-IF section 16.

Although the invention has been described in part by making detailed reference to certain specific embodiments, such details is intended to be instructive rather than restrictive. It will be appreciated by those skilled in the art that many variations may be made in the structure and mode of operation without departing from the spirit and scope of the invention as disclosed in the teachings herein.

What is claimed is:

1. A settop terminal for receiving a CATV signal comprising a plurality of channels over a transmission bandwidth, each channel for carrying information; the settop terminal comprising:

means for preprocessing said CATV signal to equalize each of said plurality of channels to a desired level, said preprocessing means comprising:
means for monitoring a channel at a lower frequency of said bandwidth and a channel at a higher frequency of said bandwidth;
means for determining the signal strength at said lower and higher frequencies;
means for calculating an attenuation profile from said determination; and
means for selectively attenuating the signal strength of a channel in response to said attenuation profile; and
channel selection means for selecting one of said equalized channels;
a selectable filter having:
a plurality of bandpass filters, each bandpass filter having a different passband encompassing at least two of said equalized channels; and
means for activating in response to said channel selection means one of said bandpass filters to filter said selected channel with a bandpass filter including the frequency of said selected channel; and
means for providing, from said selected channel, a baseband signal comprising said information for output to a display.

2. The settop terminal of claim 1 wherein said preprocessing means further comprises an automatic gain control unit which adjusts the strength of said equalized channels to a predetermined level.

3. The settop terminal of claim 2 further comprising means for controlling said automatic gain control unit in response to said calculation.

4. The settop terminal of claim 1 wherein said channel selection means further comprises:

an upconverter for mixing said selected channel with an upconversion frequency to provide a high intermediate frequency;

an intermediate filter for filtering said high intermediate frequency; and a downconverter for mixing said high intermediate frequency with a downconversion frequency to provide a low intermediate frequency.

5. A method for improving performance of a settop terminal for receiving a CATV signal comprising a plurality of channels over a transmission bandwidth, each channel carrying information, the method comprising:

preprocessing said CATV signal to equalize each of said plurality of channels to a desired level, said preprocessing step comprising:

monitoring a channel at a lower frequency of said bandwidth and a channel at a higher frequency of said bandwidth;

determining the signal strength at said lower and higher frequencies;

calculating an attenuation profile from said determination; and attenuating the signal strength of a channel in response to said attenuation profile; and selecting one of said equalized channels;

selectively filtering using a plurality of bandpass filters, each filter having a different passband which includes at least two channels;

activating one of said bandpass filters in response to said selecting step to filter said selected channel with a bandass filter having a frequency range which includes the frequency of said selected channel; and providing, from said selected channel, a baseband signal comprising said information for output to a display.

6. The method of claim 5 wherein said selection step further comprises:

mixing said selected channel with an upconversion frequency to provide a high intermediate frequency;

filtering said high intermediate frequency; and mixing said high intermediate frequency with a downconversion frequency to provide a low intermediate frequency.

\* \* \* \* \*